United States Patent
Holmes et al.

(10) Patent No.: US 9,801,591 B2
(45) Date of Patent: Oct. 31, 2017

(54) FAST ITERATIVE ALGORITHM FOR SUPERRESOLVING COMPUTED TOMOGRAPHY WITH MISSING DATA

(71) Applicant: Lickenbrock Technologies, LLC, Saint Louis, MO (US)

(72) Inventors: Timothy J. Holmes, Saint Louis, MO (US); Sean M. Larkin, Saint Louis, MO (US)

(73) Assignee: Lickenbrock Technologies, LLC, St. Louis, MO (US)

( * ) Notice: Subject to any disclaimer, the term of this patent is extended or adjusted under 35 U.S.C. 154(b) by 120 days.

(21) Appl. No.: 14/529,452

(22) Filed: Oct. 31, 2014

(65) Prior Publication Data

US 2015/0125059 A1    May 7, 2015

Related U.S. Application Data (60) Provisional application No. 61/898,806, filed on Nov. 1, 2013.

(51) Int. Cl.
| | |
|---|---|
| G06K 9/00 | (2006.01) |
| A61B 6/03 | (2006.01) |
| A61B 6/02 | (2006.01) |
| A61B 6/00 | (2006.01) |
| G06T 11/00 | (2006.01) |

(52) U.S. Cl.
CPC .......... *A61B 6/032* (2013.01); *A61B 6/027* (2013.01); *A61B 6/037* (2013.01); *A61B 6/5205* (2013.01); *G06T 11/006* (2013.01); *G06T 2211/436* (2013.01)

(58) Field of Classification Search
CPC . G06T 11/006; G06T 2211/424; A61B 6/037; A61B 6/032
See application file for complete search history.

(56) References Cited

U.S. PATENT DOCUMENTS

| | | | | |
|---|---|---|---|---|
| 5,909,476 A | * | 6/1999 | Cheng | G06T 11/006 378/4 |
| 5,933,471 A | * | 8/1999 | Kalvin | G06T 5/50 378/4 |

(Continued)

OTHER PUBLICATIONS

L. A. Shepp and Y. Vardi, "Maximum Likelihood Reconstruction for Emisssion Tomography", IEEE Transactions on Medical Imagin, vol. MI-1 No. 2 Oct. 1982, p. 113-122.*

(Continued)

*Primary Examiner* — Gandhi Thirugnanam
(74) *Attorney, Agent, or Firm* — Hoffman Warnick LLC (57) ABSTRACT

Disclosed is a method, program product, and computer system that provides iterative computed tomography (CT) image reconstruction. The approach produces an image whose resolving power exceeds that of conventional algorithms, and utilizes an inner and out iterative loop, configured by ordered subsets criteria, to perform: projecting a reconstructed image; resampling a resulting calculated projection, thereby enabling super-resolution; calculating a comparison quantity with the collected projection array (e.g., sinogram); backprojecting onto a correction array a function that utilizes the comparison quantity; and generating a new reconstructed image with an operation involving the correction array.

19 Claims, 6 Drawing Sheets

(56) References Cited

U.S. PATENT DOCUMENTS

| | | | | |
|---|---|---|---|---|
| 8,058,601 | B2* | 11/2011 | Vija | G06T 5/50 250/208.1 |
| 8,103,487 | B2* | 1/2012 | Vija | G06T 11/006 703/2 |
| 8,160,340 | B2* | 4/2012 | Vija | G06T 5/002 378/4 |
| 8,175,359 | B2* | 5/2012 | O'Halloran | G01R 33/4824 382/131 |
| 8,565,860 | B2* | 10/2013 | Kimchy | A61B 5/055 250/363.01 |
| 2007/0075248 | A1* | 4/2007 | Case | G01T 1/1611 250/363.01 |
| 2009/0304150 | A1* | 12/2009 | Metzler | G01T 1/1648 378/62 |
| 2010/0054563 | A1* | 3/2010 | Mendonca | A61B 6/032 382/131 |
| 2011/0142315 | A1* | 6/2011 | Hsieh | A61B 6/032 382/131 |
| 2011/0268334 | A1* | 11/2011 | Ra | G06T 11/005 382/131 |
| 2011/0317895 | A1* | 12/2011 | Poludniowski | A61N 5/1047 382/131 |
| 2012/0232385 | A1* | 9/2012 | Hattori | G01T 1/1648 600/436 |
| 2012/0263393 | A1* | 10/2012 | Yahil | G06T 5/002 382/264 |
| 2014/0003689 | A1* | 1/2014 | Asma | G06T 11/006 382/131 |
| 2014/0194735 | A1* | 7/2014 | Panin | G06T 11/005 600/425 |
| 2014/0200848 | A1* | 7/2014 | Panin | A61B 6/037 702/179 |
| 2014/0328528 | A1* | 11/2014 | Ra | G06T 11/005 382/131 |
| 2015/0125059 | A1* | 5/2015 | Holmes | A61B 6/032 382/131 |
| 2016/0078606 | A1* | 3/2016 | Ra | G06T 11/005 382/128 |
| 2016/0106395 | A1* | 4/2016 | Hynynen | A61B 8/4494 600/431 |

OTHER PUBLICATIONS

H. M. Hudson and R. Larkin, "Accelerated Image Reconstruction Using Ordered Subsets of Projection data", IEEE Transactions on Medical Imaging, vol. 13, No. 4, 1994, p. 601-609.*

A. DePierro and M. Yamagishi, "Fast EM-like Methods for Maximum "A Posteriori" Estimates in Emission Tomography", IEEE Transactions on Medical Imaging, vol. 20 No. 4, Apr. 2001, p. 280-288.*

Yokoi, T. et al, "Performance evaluation of OSEM reconstruction algorithm incorporating three-dimensional distance-dependent resolution compensation for brain SPECT: a simulation study." Ann Nucl Med. Feb. 2002;16(1):11-8.*

Alessio, A. et al, "Modeling and Incorporation of System Response Functions in 3D Whole Body PET", http://faculty.washington.edu/aalessio/papers/alessioSRF_MIC04.pdf, p. 1-5.*

Erdogan et al., Ordered Subsets Algorithms for Transmission Tomography, Phys. Med. Biol. 44 1999, pp. 2835-2851.

Fessler, Statistical Image Reconstruction Methods for Transmission Tomography, University of Michigan 2000, from Retrieved http://proceedings.spiedigitallibrary.org, pp. 1-70.

Guan et al., A Projection Access Order for Speedy Convergence of ART (Algebraic Reconstruction Technique): a Multilevel Scheme for Computed Tomography, Phys. Med. Biol. 39 1994, pp. 2005-2022.

Herman et al., Algebraic Reconstruction Techniques Can Be Made Computationally Efficient, IEEE Transactions on Medical Imaging, vol. 12, No. 3, Sep. 1993, pp. 600-609.

Hudson et al., Accelerated Image Reconstruction Using Ordered Subsets of Projection Data, IEEE Transactions on Medical Imaging, vol. XX, No. X,1994, pp. 100-108.

Kamphuis et al., Accelerated Iterative Transmission CT Reconstruction Using an Ordered Subsets Convex Algorithm, IEEE Transactions on Medical Imaging, vol. 17, No. 6, Dec. 1998, pp. 1101-1105.

Lange, Convergence of EM Image Reconstruction Algorithms with Gibbs Smoothing, IEEE Transactions on Medical Imaging, vol. 9, No. 4, Dec. 1990, pp. 439-446.

Lange et al., Globally Convergent Algorithms for Maximum a Posteriori Transmission Tomography, IEEE Transactions on Image Processing, vol. 4, No. 10, Oct. 1995, pp. 1430-1438.

Li et al., Implementation of an Accelerated Iterative Algorithm for Cone-beam SPECT, Phys. Med. Biol. 39, 1994, pp. 643-653.

Manglos et al., Transmission Maximum-likelihood Reconstruction with Ordered Subsets for Cone Beam CT, Phys. Med. Biol. 40, Mar. 1995, pp. 1225-1241.

Miller et al., The Role of Likelihood and Entropy in Incomplete-Data Problems: Applications to Estimating Point-Process Intensities and Toeplitz Constrained Covariance, Proceedings of the IEEE, vol. 75, No. 7, Jul. 1987, pp. 892-907.

Murphy et al., Pose Estimation of Known Objects During Transmission Tomographic Image Reconstruction, IEEE Transactions on Medical Imaging, vol. 25, No. 10, Oct. 2006, pp. 1392-1404.

Nuyts et al., Iterative Reconstruction for Helical CT: a Simulation Study, Phys. Med. Biol. 43, 1998, pp. 729-737.

Ollinger, Maximum-Likelihood Reconstruction of Transmission Images in Emission Computed Tomography via the EM Algorithm, IEEE Transactions on Medical Imaging, vol. 13, No. 1, Mar. 1994, pp. 89-101.

O'Sullivan et al., Alternating Minimization Algorithm for Dual Energy X-Ray CT, Washington University and Virginia Commonwealth University, 2004, 4 pages.

O'Sullivan et al., Alternating Minimization Algorithms for Transmission Tomography, Washington University, May 2006, pp. 1-28.

Rashed et al., Iterative Region-of-Interest Reconstruction from Truncated CT Projection Data Under Blind Object Support, Medical Imaging Technology vol. 27, No. 5, Nov. 2009, pp. 321-331.

Snyder et al., Deblurring Subject to Nonnegativity Constraints, IEEE Transactions on Signal Processing, vol. 40, No. 5, May 1992, pp. 1143-1150.

Snyder et al., Deblurring Subject to Nonnegativity Constraints When Known Functions are Present with Application to Object-constrained Computerized Tomography, IEEE Transactions on Medical Imaging, vol. 20, No. 10, Oct. 2001, pp. 1009-1017.

Hamelin et al., Design of Iterative ROI Transmission Tomography Reconstruction Procedures and Image Quality Analysis, Med. Phys. 37 (9), Sep. 2010, pp. 4577-4589.

Wang et al., Iterative Deblurring for CT Metal Artifact Reduction, IEEE Transactions on Medical Imaging, vol. 15, No. 5, Oct. 1996, pp. 657-664.

Zhang et al., Two-dimensional Iterative Region-of-Interest (ROI) Reconstruction from Truncated Projection Data, Med. Phys. 34 (3), Mar. 2007, pp. 935-944.

* cited by examiner

FAST ITERATIVE ALGORITHM FOR SUPERRESOLVING COMPUTED TOMOGRAPHY WITH MISSING DATA

PRIORITY

This application claims priority to U.S. provisional application 61/898,806, EM ALGORITHM FOR NONDESTRUCTIVE TESTING WITH X-RAY COMPUTED TOMOGRAPHY, filed on Nov. 1, 2013, the contents of which are hereby incorporated by reference.

This invention was made with Government support under contract FA9300-13-C-2014 awarded by the U.S. Air Force. The Government has certain rights in the invention. Distribution A: Approved for Public Release; Distribution Unlimited. PA#17180.

BACKGROUND

The present invention relates to an iterative image reconstruction algorithm, which is a variant of an expectation-maximization (EM) algorithm for computed tomography applied to many applications that include medicine and nondestructive testing. It applies to a variety of types of CT, including transmission CT and emission CT. Transmission CT includes x-ray CT. Emission CT includes positron emission tomography (PET) and single photon emission computed tomography (SPECT).

Computed tomography (CT) is a technique for imaging cross-sections of an object using a series of X-ray measurements taken from different angles around the object. It has been widely applied in diagnostic medicine and industrial non-destructive testing. Two dimensional (2D) and three dimensional (3D) computed tomography are currently used to, e.g., provide defect detection, information about material properties or metrology of manufactured components and materials, such as metal castings.

The expectation-maximization (EM) algorithm refers to variants of an iterative computed tomography (CT) image reconstruction algorithm, first introduced in the 1980's for positron emission tomography (PET). The term EM algorithm strictly refers to the iterative mathematical formalism for defining the objective function and iterative optimization scheme when the data collection system have specific physical characteristics for which a type of Poisson process model is generally appropriate. Strictly speaking, the term EM algorithm applies to many parameter estimation problems and not just CT or PET. Variants to the PET EM algorithm have been designed for single photon emission CT (SPECT), for 2D and 3D deconvolution with light microscopy, telescopic imaging through atmospheric turbulence and general optical imaging deconvolution. With x-ray CT and other forms of transmission tomography there are many forms of iterative reconstruction that are called EM algorithms because they originate from the strict mathematical EM formalism. Even so, some of these so-called EM algorithms have a different form than the one originally developed for PET. In the embodiment described here, the predominant steps in the algorithm were originally designed for PET, even though they are being applied to transmission CT here, but it is still called the EM algorithm here, and perhaps loosely so, because it has resemblance to the same algorithm despite the fact that the physical underpinnings are different.

One historical challenge with the various EM algorithms for CT, and other iterative algorithms, has been long processing times. It is not unusual for the processing time to take on the order of several hours. Accordingly, their use in CT applications has been limited.

SUMMARY

Disclosed is a system, method and program product for implementing an improved EM algorithm for usage with nondestructive testing x-ray computed tomography (CT). The improved algorithm applies to many other forms of both transmission and emission CT. It applies to other applications besides nondestructive testing, including medicine, biology, medical research and other life-science research. According to one aspect of the present invention, a method for reconstructing an image implemented on a computing system is provided, comprising: inputting a collected projection array $p(r,\theta)$ produced from a CT system (where r and $\theta$ are the indices of the radial and angular coordinates of the CT system) imaging an object defined with a multi-dimensional image function $f(\bar{x})$ (where $\bar{x}$ is a vector notation of the index of the 2D or 3D spatial coordinate); generating an initial reconstructed image $f_R(\bar{x})$; utilizing an iterative loop to perform: projecting the reconstructed image $f_R(\bar{x})$ onto a projection array $p_R(r,\theta)$; calculating a comparison quantity $q(r,\theta)$, calculated from the projection array $p_R(r,\theta)$ and the collected projection array $p(r,\theta)$; backprojecting onto a correction array $b(\bar{x})$ a function that utilizes the comparison quantity $q(r,\theta)$; generating a correction factor based on the correction array $b(\bar{x})$; generating a new reconstructed image $f_R(\bar{x})$ that modifies a previous reconstructed image with an operation involving the correction array $b(\bar{x})$; wherein a spatial sampling of pixels in the new reconstructed image is enhanced to a finer resolution; and wherein a smoothing operation is applied to the projection array $p_R(r,\theta)$; and outputting a final image $f_R(\bar{x})$.

In a second aspect, the invention provides program product stored on a computer readable medium, which when executed by a computer system, reconstructs an image implemented, comprising: program code for inputting a collected projection array $p(r,\theta)$ produced from a CT system imaging an object defined with a multi-dimensional image function $f(\bar{x})$; program code for generating an initial reconstructed image $f_R(\bar{x})$; program code for implementing an iterative loop to perform: projecting the reconstructed image $f_R(\bar{x})$ onto a projection array $p_R(r,\theta)$; calculating a comparison quantity $q(r,\theta)$, calculated from the projection array $p_R(r,\theta)$ and the collected projection array $p(r,\theta)$; backprojecting onto a correction array $b(\bar{x})$ a function that utilizes the comparison quantity $q(r,\theta)$; generating a correction factor based on the correction array $b(\bar{x})$; generating a new reconstructed image $f_R(\bar{x})$ that modifies a previous reconstructed image with an operation involving the correction array $b(\bar{x})$; wherein a spatial sampling of pixels in the new reconstructed image is enhanced to a finer resolution; and wherein a smoothing operation is applied to the projection array $p_R(r,\theta)$; and program code for outputting a final image $f_R(\bar{x})$.

In a third aspect, the invention provides a computer system for reconstructing an image implemented on a computing system, comprising: a system for inputting a collected projection array $p(r,\theta)$ produced from a CT system imaging an object defined with a multi-dimensional image function $f(\bar{x})$; a system for generating an initial reconstructed image $f_R(\bar{x})$; a system for utilizing an iterative loop to perform: projecting the reconstructed image $f_R(\bar{x})$ onto a projection array $p_R(r,\theta)$; calculating a comparison quantity $q(r,\theta)$, calculated from the projection array $p_R(r,\theta)$ and the collected projection array $p(r,\theta)$; backprojecting onto a correction array $b(\bar{x})$ a function that utilizes the comparison quantity $q(r,\theta)$; generating a correction factor based on the correction array $b(\bar{x})$; generating a new reconstructed image $f_R(\bar{x})$ that modifies a previous reconstructed image with an operation involving the correction array $b(\bar{x})$; wherein a spatial sampling of pixels in the new reconstructed image is enhanced to a finer resolution; and wherein a smoothing operation is applied to the projection array $p_R(r,\theta)$; and a system for outputting a final image $f_R(\bar{x})$.

In a fourth aspect, the invention provides a method for reconstructing an image, comprising: inputting a collected projection array produced from a CT system imaging an object defined with a multi-dimensional image function; generating an reconstructed image based on an initial guess; separating indices of the collected projection array into subsets; processing each subset, including: projecting the reconstructed image onto a reconstructed projection array corresponding to a current subset of indices; calculating a comparison quantity for values associated with the current subset of indices; backprojecting onto a correction array a function that utilizes the comparison quantity; and generating an updated reconstructed image that modifies a previous reconstructed image based on the correction array; and outputting a final reconstructed image.

BRIEF DESCRIPTION OF THE DRAWINGS

These and other features of this invention will be more readily understood from the following detailed description of the various aspects of the invention taken in conjunction with the accompanying drawings.

The drawings are merely schematic representations, not intended to portray specific parameters of the invention. The drawings are intended to depict only typical and simplified embodiments of the invention, and therefore should not be considered as limiting the scope of the invention. In the drawings, like reference numbering represents like elements.

DETAILED DESCRIPTION

Described herein is a system, method and program product for implementing a variant of an EM algorithm for usage with computed tomography (CT). Part of the invention involves a scheme that uses ordered-subsets and is referred to herein also as a fast EM ordered-subsets (FEMOS) algorithm. Aspects of the invention involve a scheme that produces a resolving power, called super-resolution, which is better than CT systems conventionally provide. Part of the invention involves a scheme for dealing with truncated, missing, corrupt or invalid data, referred to herein as the missing data algorithm. There are many categories of CT systems with which these algorithms may be used. The algorithms may be used with CT systems that use the principle of projections, where the collected dataset may be described as a set of line integrals, called projections, of the 2D or 3D quantity, called an image, which is being reconstructed. This includes, but is not limited to, x-ray CT, positron emission tomography, single-photon emission computed tomography, CT using subatomic particles, such as neutrons, phase-contrast x-ray CT and electron tomography using a series of tilted projections. CT systems have many geometries that work according to both two-dimensional (2D) and three-dimensional (3D) mathematical principles. These include geometries such as parallel beam (FIG. 8*a*), fan beam (FIG. 8*b*), cone beam (FIG. 8*c*), spiral scanning, rotate/traverse scanning (e.g., Generation-2), and others.

Hybrid schemes may also be utilized including those that combine the spiral and cone-beam geometries (i.e., spiral cone-beam) and those that combine the fan-beam and parallel-beam geometry. Many systems perform some form of 3D CT by successively translating either the specimen or the scanning mechanism along the z axis while imaging at various planes and then stacking the resulting 2D images to produce a 3D volumetric image.

Illustrative applications include nondestructive testing, quality inspection, research and development, and other activities in such fields as the material science, manufacturing, aircraft, aerospace, automobile, heavy equipment and other industries. The applications also include medicine, medical science, veterinary medicine, small animal imaging, biology, materials, manufacturing and other fields.

Figure 1:
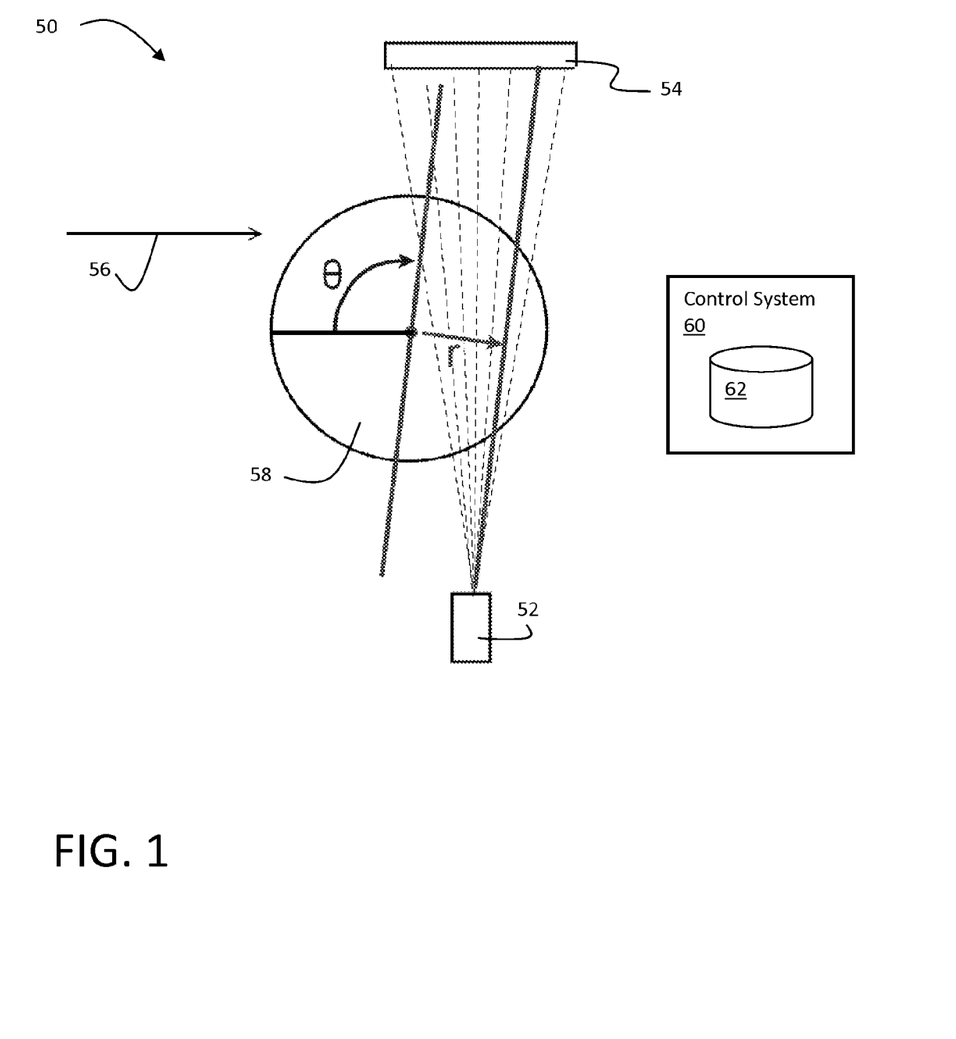
FIG. 1 depicts a CT system in accordance with embodiment of the present invention.
Figure 8A:
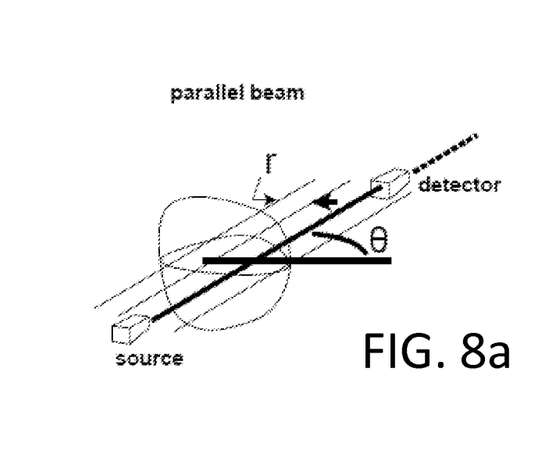
FIGS. 8*a*, 8*b* and 8*c* illustrate schemes of CT geometries for the arrangement among the radiating source, detector and imaged object.
Figure 8B:
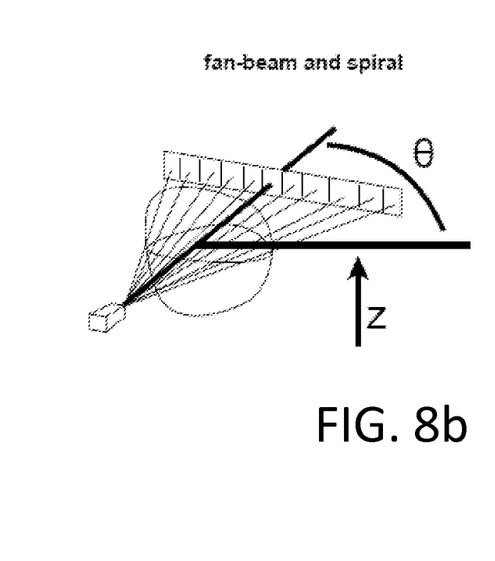
Figure 8C:
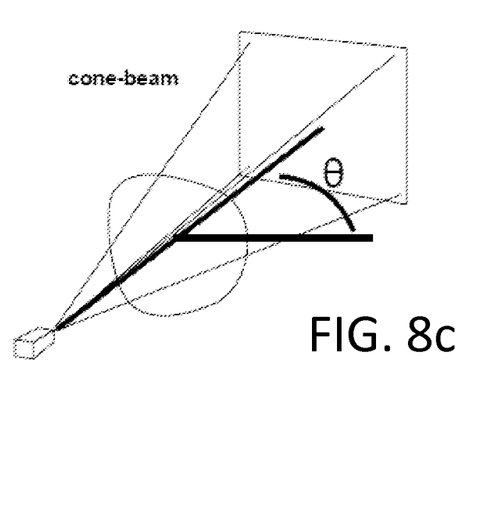

FIG. 1 illustrates a transmission CT system. X-ray CT is a form of transmission CT. Positron emission tomography, single photon emission tomography and others are forms of emission CT (not shown). As shown in FIG. 1, a CT system 50 is shown for capturing CT data and processing the data to produce CT images 62. The nondestructive testing CT system 50 generally includes a movable turntable 58, shown in a top down view, on which a specimen (not shown) to be imaged is placed. Medical and other forms of CT move the x-ray source and detector and hold the specimen (e.g., patient, human or animal subject) stationary, but the diagram shown still applies since this difference in configuration only changes the frame of reference. There are various scanning sequences. In one scheme, sometimes called the rotate-and-traverse scheme, the angle is set and the turntable is traversed to successive horizontal positions. At each horizontal position the x-ray source is pulsed while collecting the projection data at each of these horizontal positions. The angle is then incremented to another position (e.g., at increments equal to or near the angle size of the fan) and the traverse sequence is repeated. In another scheme the turntable 58 is traversed into position as shown by arrow 56, and then rotates while the series of fan projections are collected. An X-ray source 52 beams X-rays through the object at different radial positions r, with the resulting X-ray beams being detected by X-ray detector 54. In a rudimentary form the x-ray detector may be a single detector as in FIG. 8*a*. More commonly it will be a detector array assembly, as in FIGS. 8*b* and 8*c*, for recording magnitudes of multiple rays simultaneously. A linear detector array and a 2D flat-panel array of simultaneous detectors are illustrated in FIGS. 8*b* and 8c, respectively. A control and acquisition system 60 controls the operation and collects the resulting unprocessed CT data 62. This unprocessed data encodes and records information that will be referred to here as metadata. The metadata encodes and records the positions, orientations, configurations and settings of the x-ray source, detector array, turntable, collimators, detection electronics, recording electronics, and other data-collection components. The metadata may also include parameters of the detection electronics, such as detection sensitivities associated with individual detector elements, which may be determined from calibration processes. The unprocessed data also records the measurements of x-ray intensities that originate from the detector array. Processing of these unprocessed CT data recordings transforms them into a digital form, commonly called a sinogram, which is compatible with image-reconstruction algorithms. A logarithm operation, also called inverse-exponentiation, reverses the effects of the exponential decay law known as Beer's law. Processing sometimes includes corrections of the data for adverse effects such as nonuniform in sensitivity of x-ray detectors, nonuniform spatial sampling, amplifier gains and other settings, adjustments and parameters of the control and acquisition system. After the preprocessing is completed, the projection $p(r,\theta)$ is recorded and stored. When referring to the parallel-beam and fan-beam geometries, 2D imaging and 2D data collection (FIGS. 8a and 8b) the projection array is commonly called the sinogram. It will be called the projection array, here, to generally encompass 3D imaging and the many other geometries.

The projection array is expressed here with the notation $p(r,\theta)$. In the simpler 2D geometries the meanings of r and $\theta$ are illustrated in FIGS. 1 and 8a. Here, they more strictly refer to indices that point to the spatial parameters. In the complex 3D geometries $\theta$ refers to the angular position or orientation of the scanning mechanism in relation to the specimen while r refers to the generalized index that points to the specific ray associated with the source and sensing element in the detector array. A resulting reconstructed image $f_R(x,y)$ or $f_R(x,y,z)$ can be obtained by applying an image reconstruction algorithm to the projection array, where x, y and z are indices of the Cartesian spatial coordinates, $f_R(x,y)$ is the reconstructed 2D image and $f_R(x,y,z)$ is the reconstructed 3D image for applications such as cone-beam, spiral, certain forms of fan-beam and Generation-2 imaging where 2D image slices are stacked to form a 3D volume image. To make expressions simpler, we alternatively denote the 2D and 3D coordinates as a vector using the $\bar{x}$ with an overbar which corresponds to x, y and x, y, z, respectively. The reconstructed image represents an estimation of the underlying 2D or 3D image $f(\bar{x})$ that caused the projection data $p(r,\theta)$. In the case of x-ray CT this underlying image is a representation of the 2D or 3D distributed attenuation coefficient of the material being imaged. In other types of CT it represents other quantities, such as a density of radioactive substance in the cases of PET and SPECT. Despite the fact that $f(\bar{x})$ is the true representation of the image, it is an unknown quantity, and will never be known with perfect accuracy. The production of $f_R(\bar{x})$ is an attempt to knowing $f(\bar{x})$, but it is understood that it has practical errors due to resolving power, noise, artifacts and other factors.

Although FIG. 1 generally describes a parallel beam CT implementation, it is understood that other CT arrangements may also be utilized, e.g., fan-beam, cone-beam, spiral, hybrids thereof, etc. In the parallel beam case, r is an index that provides the radial distance coordinate of the parallel beam geometry and the $\theta$ index points to the rotation angle coordinate. In the fan-beam and cone-beam cases, r is an index that identifies the ray in the fan or cone, respectively, and $\theta$ indexes to the rotation angle of the fan or cone as a unit, respectively. In the spiral scanning cases, r is an index that identifies the specific ray for a given source, detector and specimen orientation and $\theta$ represents the index to the individual positioning of the source, detector and specimen in relation to one another in the spiral data-collection series.

Figure 2:
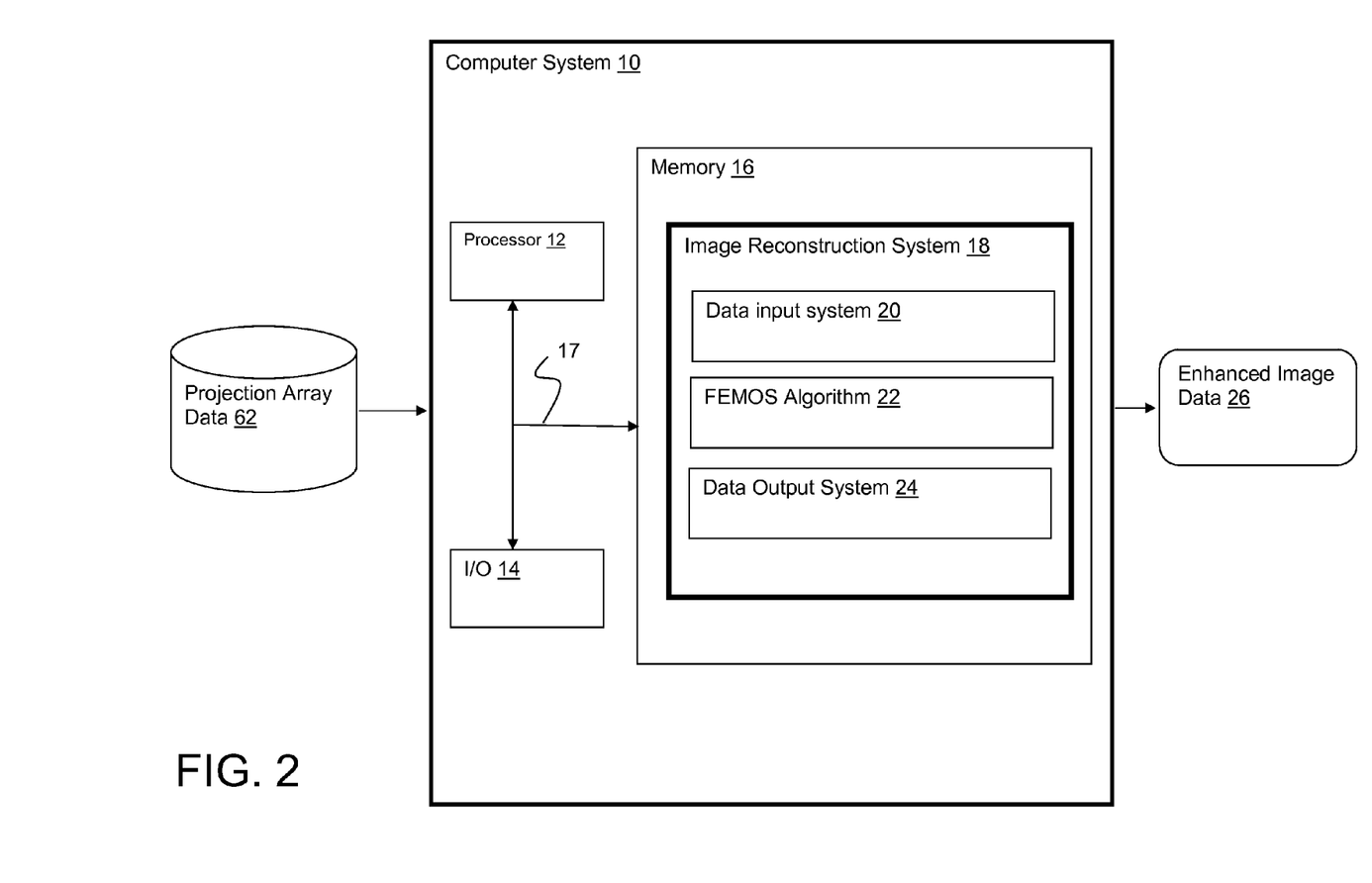
FIG. 2 depicts a computer system having an Image reconstruction system in accordance with embodiments of the present invention.

FIG. 2 depicts a computer system 10 having an image reconstruction system 18 that utilizes a FEMOS 22 and other algorithms described herein to process projection array data 62 to create enhanced reconstructed image data 26. The reconstructed images are enhanced because, typically, they have improved contrast, less severity in artifacts, improved resolving power or other image quality character compared to images reconstructed by conventional algorithms, such as filtered backprojection (FBP), FBP variants, such as the Feldkamp algorithm, and previous renditions of the EM algorithm. Image reconstruction system 18 includes a data input system 20 for receiving data 62, FEMOS, superresolution and missing data algorithms 22 for processing data 62, and data output system 24 for outputting the enhanced image data 26. The enhanced image data 26 may be saved to storage, displayed on a display device, further processed, etc.

Figure 3:
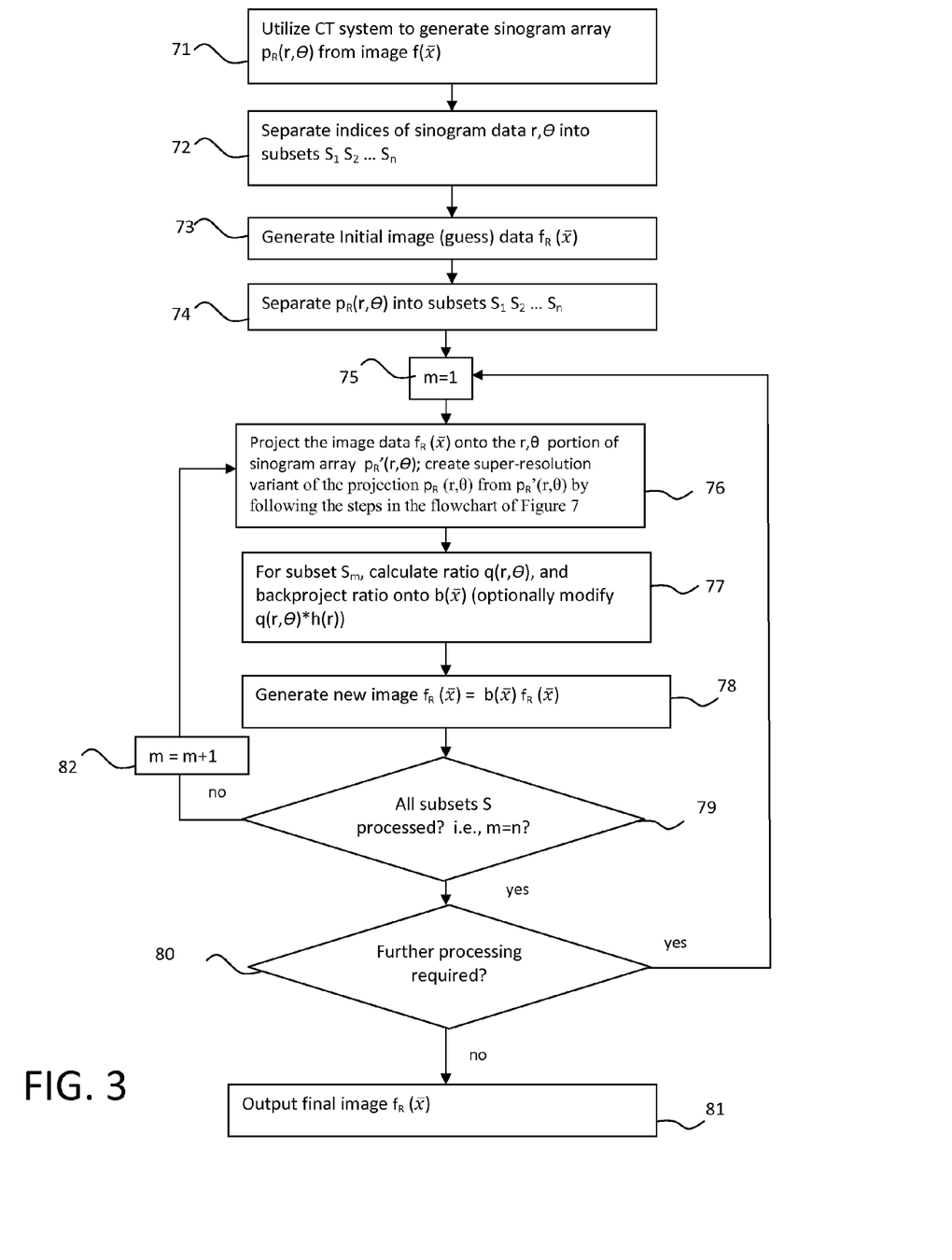
FIG. 3 depicts a flow diagram showing an implementation of the FEMOS algorithm with super-resolution in accordance with embodiments of the present invention.

FIG. 3 depicts a flow diagram describing an illustrative embodiment of the FEMOS algorithm with super-resolution, which is a variant of the EM algorithm that utilizes ordered subsets. This embodiment is described using a parallel beam geometry. However, generalizations to it and minor changes to it will accommodate other types of CT geometry. The projection rays, their coordinates, the subsets, the projections and the algorithm can be generalized and thereby defined for virtually any CT architecture, including fan-beam, cone-beam, spiral, hybrids thereof and others. For other CT architectures, the spatial mathematical coordinates corresponding to the indices r and $\theta$ need to be reformulated for the coordinate system of the architecture.

At 71, a CT system generates a projection array $p(r,\theta)$ from an object being imaged, in which $f(\bar{x})$ represents the ideal noise-free image that is an unknown quantity to be reconstructed. An example is illustrated with the Rapiscan ICT 2500 high energy CT system that images large aerospace components. This is a Generation 2 system, which uses a fan-beam rotate and traverse configuration like the one shown in FIG. 8b. The upstream projection data are prepocessed for many considerations, including Beer's law, and they are rearranged into parallel-beam data so that $p(r,\theta)$ is that of a parallel beam geometry. In this way, the Rapiscan ICT 2500 model represents a hybrid that is both a fan-beam and parallel-beam system because, depending upon where one looks within the processing pipeline, the data are arranged for either a fan-beam or parallel beam geometry. Many fan-beam systems can have their datasets rearranged into a parallel beam configuration, so it is convenient to focus the description on the parallel beam geometry. A typical projection array contains 720 angles, equally spaced over 180 degrees, 2048 samples along the r dimension with the space between the samples, called bin size, being 0.904 millimeters.

At 72, sampling parameters are set. Conventionally, it is common to set the spatial size of each square pixel to be the same as, or near, the projection array bin size and to set the number of pixels in either direction to be the number of projection bins. Similarly, the pixel size in fan-beam, cone-beam and other geometries is conventionally set to be at or near the distance between projection rays near the center of the image plane or volume. In this case, the image then has a size of 2048×2048 (i.e., 2048 pixels along the x and y dimensions) and a 2048×0.904=1851.4 mm field size. The term super-resolution refers to the capability to view fine details in the image with a resolving power that is better than conventional limits. Doing so algorithmically is accomplished by several provisions about the chosen pixel size and the utilization of smoothing operators within the iteration. When super-resolution is desired, generally, a smaller pixel than that dictated by normal convention is required. Experimentation has shown that these pixels may be set to be as small as ⅓ conventional sizes, resulting in a 6144×6144 image having the same 1851.392 field size and 0.904/3=0.301 mm pixels.

An initial image (i.e., a first guess) is generated as $f_R(\bar{x})$ at 73. There are many ways to design a first guess. Common effective first guesses include the following: a constant image, where every pixel has the same value. This value may be made equal to, for example, $\bar{p}/(N_x \Delta x)$ where $\bar{p}$ is the average projection-array value, averaged over all r and θ, $N_x$, is the number of pixels along one of the sides of the image and $\Delta x$ is the pixel size. An image formed by a conventional image reconstruction such as filtered backprojection is often suggested as a choice of first guess, thinking that an already reconstructed image will produce an effective FEMOS reconstruction with fewer iterations. However, experimentation has shown that this first guess is often ineffective because it can contain strong edges due to artifacts and noise. Undesirable strong edges do not disappear easily as the iterations proceed with the FEMOS algorithm, nor with other variants of the EM algorithm. A better first guess is one with no edges or, at least, smooth edges. Therefore, an already reconstructed image as a first guess is generally inadvisable, and unnecessary considering the speed of the FEMOS algorithm.

At 74, indices of the projection data r,θ are separated into ordered subsets $S_1, S_2 \ldots S_n$. In other words, the projection array p(r,θ) is separated into subsets according to these defined indices r and θ. The r,θ indices and projection data may be separated into subsets in any manner, although a manner is described later that is optimal for increasing speed of progress of the algorithm. As will be explained below, the algorithm is decomposed in a way that only a specifically chosen subset of the projection array is operated upon at any given time, which defines an inner iteration. Doing so causes an acceleration of the progress of the algorithm and thereby dramatically shorter computation time. The sequence order, in which these subsets are executed, is an important specification that affects whether or not artifacts may occur and, in turn, affects the amount of algorithm acceleration that can be achieved.

The subsets are defined as sets of projection rays indexed by r,θ, and are equivalently defined as sets of the index pair r,θ. This index pair may be considered to be a vector with two elements r and θ. Furthermore, since r and θ may each contain more than one element, as could be the case for the conebeam and spiral geometries, the r,θ index may be thought of as an even higher dimensional vector. Strictly speaking, the subsets are of these vector indices. These subsets may be defined in any way. In some approaches, subsets are decomposed only by the angle indices θ so that each subset has a full complement of possible values of r. The illustrations here assume this approach.

When the angles comprise the subsets in the cases of fan-beam and conebeam, one way to define the angle is that of the nominal angle illustrated in FIGS. 8b and 8c. In those cases the nominal angle defines the orientation of the source and detector in relation to the object. In this illustration θ is the index of the angle of the central ray in the fan or cone. The many rays collected at the nominal angle are indexed by r and are at different physical orientation angles because of their position in the fan or cone, but they still have the same nominal angle.

Figure 4:
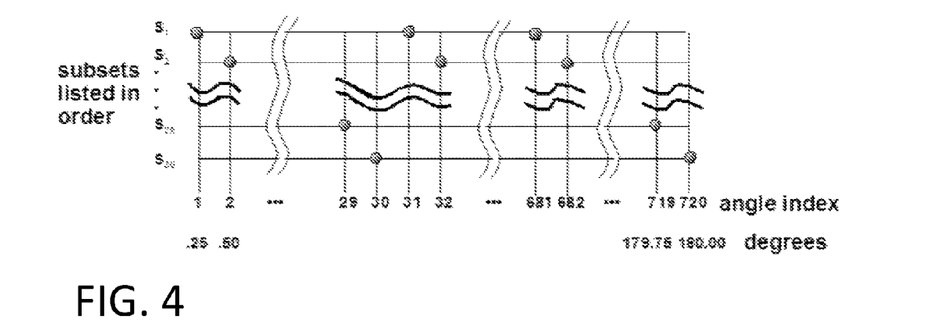
FIG. 4 depicts a scheme for selecting ordered subsets in accordance with embodiments of the present invention.

In one approach for configuring the subset angles, the collection of angles in a given subset are equally and maximally spaced from each other, thereby achieving a form of balance. Experience has shown that doing so avoids certain streak artifacts that may appear in the reconstructed image. FIG. 4 is a graphical illustration of the subsets for one example of the subset choices that follow this idea, assuming 720 angles spaced evenly over 180 degrees. The dots mark the angles that are in each designated subset $S_1$, $S_2$, $S_3$ . . . . With 720 angles decomposed into 30 subsets, the following angles are included in each subset, i.e., Subset $S_1$=[0, 26, 52 . . . 154] degrees; Subset $S_2$=[0.25, 26.25, 62.25, . . . 154.25], Subset $S_3$=[0.5, 26.5, 62.5, . . . 154.5] . . . , Subset $S_{30}$=[7.25, 33.25, 59.25, . . . 161.25]. The angles are evenly spaced by 26 degrees. The first angle of each subset is the adjacent angle to the first angle of the prior subset.

Figure 5:
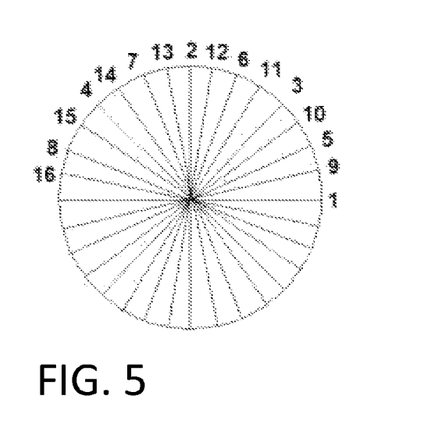
FIG. 5 depicts a further scheme for selecting the sequence of first angle in the ordered subsets in accordance with embodiments of the present invention.

Despite the advantage of the above approach, experiments have shown that it has a limit below which the number of subsets must remain. Otherwise the reconstructed image has streak artifacts. In limited experiments with a specific CT scanner, a configuration with 720 angles, and types of object, this number was 30 and, thereby, the number of angles was limited to 24 and higher. In further embodiments, this problem is avoided. Subsets may be ordered so that the first angle in subsequent subsets is maximally spaced from the first angle of the prior subset in the order, and this effectively avoids these artifacts. A scheme like this is illustrated in FIG. 5, which illustrates the ordering of the angle positions, over a 180 degree range, of the first angle of subsequent subsets. It is assumed in these examples that the angles within each subset are maximally spaced from each other, at least to a reasonable approximation or as best as can be practically achieved, similar to FIG. 4. Each subset (shown as numerals along the circumference) is defined by one angle (i.e, the first angle in the subset) and its full complement of radial projection coordinates indexed by r. In other words, it is a projection at a given nominal angle.

The main objective is to avoid artifacts by having as much distance as possible between nominal angles adjacent to one another in the order sequence. Literature has suggested the reasoning that this distance is desirable in order to minimize the correlation between adjacent projections. This reasoning does not follow a mathematical foundation, but experimentation has shown that keeping these distances as large as possible eliminates the artifacts while providing for the capability to increase the number of subsets. In this scheme, the first two angles in the sequence (1 and 2) are 90 degrees apart, which is the largest possible distance with 180 available degrees. The next two angles are chosen to be maximally distant from these first two and from one another. In doing so, they are 45 degrees from one another and 22.5 degrees from the prior angles. The next four angles are chosen so that they are distant from the prior two and from all prior angles, by making them 22.5 degrees from one another and 11.25 degrees from the prior angles. Then the next eight angles are chosen using a similar criterion of maximizing the distance from each other and from the prior angles. This pattern continues until the complement of angles is completed. When the number of angles is not divisible by two or another number that is necessary to meet this pattern perfectly, the angle that is chosen is the one that is closest to what a precise calculation would specify. An approximation to this algorithm may work as well as the precise algorithm. Precision in selecting these angles is not required.

Figure 6:
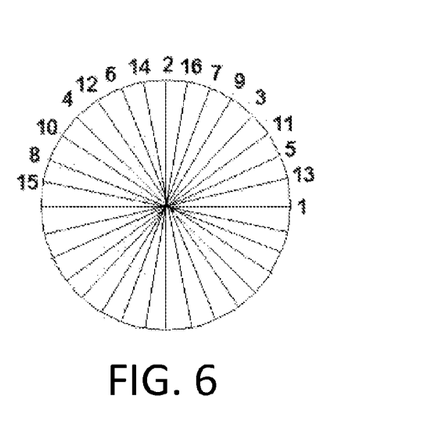
FIG. 6 depicts a further scheme for selecting the sequence of first angle in the ordered subsets in accordance with embodiments of the present invention.

There are variations this type of scheme. Some will more rigorously achieve the objective of balancing the angles and having large distances between adjacent angles in the order sequence. FIG. 6 shows another one that is more rigorous for maximizing the distance with angles that are nearby in the order sequence. Each angle is chosen so that it is maximally distant from the angle just prior to it (i.e., as close to 90 degrees as possible from the prior selection) and maximally distant from the previously selected angle. For example, note that angle number 6 is maximally distant from angle 5 and maximally distant from the nearest possible angle in the remainder of previous angles (i.e., 1-4). The distance is defined in a modulo-arithmetic sense, where 180 degrees is equivalent to 0 degrees. Another way to approach this configuration is to define the distance by a modulo 360-degree number, which may be appropriate for certain types of cone-beam and spiral CT. The order in FIG. 6 is not the only order that would satisfy this criterion. It is not required to precisely and accurately meet this criterion. An approximation to it would work. This scheme was designed as one way to avoid having adjacent angles in the sequence order from being close to one another. The numbers and angle selections do not have to be precise, and in some cases they cannot be precise because the number of angles and the spacing of the angles may not be regular.

By using this type of "maximum distance" scheme, the artifacts that can occur with the scheme in FIG. 4 are avoided so the number of subsets is able to be increased. In one embodiment, the total number of subsets may be equal to the total number of angles, e.g., 720 in the above case, and each subset contains just one angle.

More complex schemes that more rigorously maximize the distance between an angle and its neighbors in the ordered sequence could be implemented. For example, one may first maximize the distance of the 118-th angle to the 117-th angle. When more than one possible angle meets this criterion, the choice may be made by having a secondary criterion to maximize its distance to the 116-th angle, followed by a tertiary criterion of maximizing the distance to the 115th angle, and so on. The idea behind doing so is to have the most balance with the angles that were selected nearby in the sequence. Experimentation suggests that keeping adjacent angles in the order sequence away from each other is beneficial, although it is unclear to what lengths the complexity of the scheme must go without testing with specific specimens.

It is noted that the capability to increase the number of subsets dramatically increases the computation speed. This happens because, to a rough extent, the image reconstruction makes similar progress in an inner iteration regardless of the number of angles, but the amount of time to compute an inner iteration is roughly proportionate to the number of angles. Because the number of subsets is inversely proportional to the number of angles, to a rough extent, the amount of progress the outer iteration makes is roughly proportionate to the number of subsets and inversely proportionate to the number of angles per subset. Yet, the amount of time to calculate the outer iteration is roughly similar regardless of the number of subsets or angles per subset. Hence, there is an overall dramatic computational speed increase that is roughly proportional to the number of subsets and numbers like 720 angles with 720 subsets cause a significant speed increase.

As implied by the above explanation, experimentation has shown that the fastest convergence is achieved when the number of subsets equals the number of angles, so that each subset just contains one angle. There could be reasons for avoiding this configuration, however. For example, experimentation has shown that this condition can cause unstable results when there is considerable noise in the data. Such situations occur routinely with radionuclide imaging as with PET and SPECT. It can occur with nondestructive testing x-ray CT due to large, dense material or low x-ray energies. Even in cases that are considered to have low noise, there can still be a low overall signal-to-noise level in the background areas of the image or projection array (i.e., those areas that are otherwise expected to have near-zero values). To avoid such instabilities, or other issues, the number of subsets may be varied from one outer iteration to the next. The larger the number of angles per subset, and thereby the smaller the number of subsets, the better is the robustness against noise. To take advantage of both the robustness of a smaller number of subsets and the speed of the larger number of subsets, one may start with a larger number of subsets in the first outer iteration, and then decrease them as the outer iterations proceed or start with a small number of subsets and then increase them as the outer iterations proceed. Experimentation has shown this scheme to be effective in reducing background noise (in near zero areas of the image). There may be other situations where it is beneficial to start with a large number of subsets in the first outer-iteration and then increase the number of subsets in later iterations.

Next the iterative portion of the algorithm is executed, which includes an inner loop (i.e., iteration) for processing subsets, initialized at m=1 (shown with reference number 75), and an outer loop (i.e., iteration). Within the inner loop, at 76, the image data $f_R(\overline{x})$ is projected onto the r,θ portions of the projection array $p_R(r,\theta)$ that define the m-th subset. The sampling, with respect to r, for $p_R(r,\theta)$, is chosen to be the same as or near the pixel spacing of $f_R(\overline{x})$. Thereby, when super-resolution is desired, the r spatial sample sizes (also called projection bin sizes) in $p_R(r,\theta)$ may be smaller (i.e., have a higher sampling rate) than the collected projection array $p(r,\theta)$.

Figure 7:
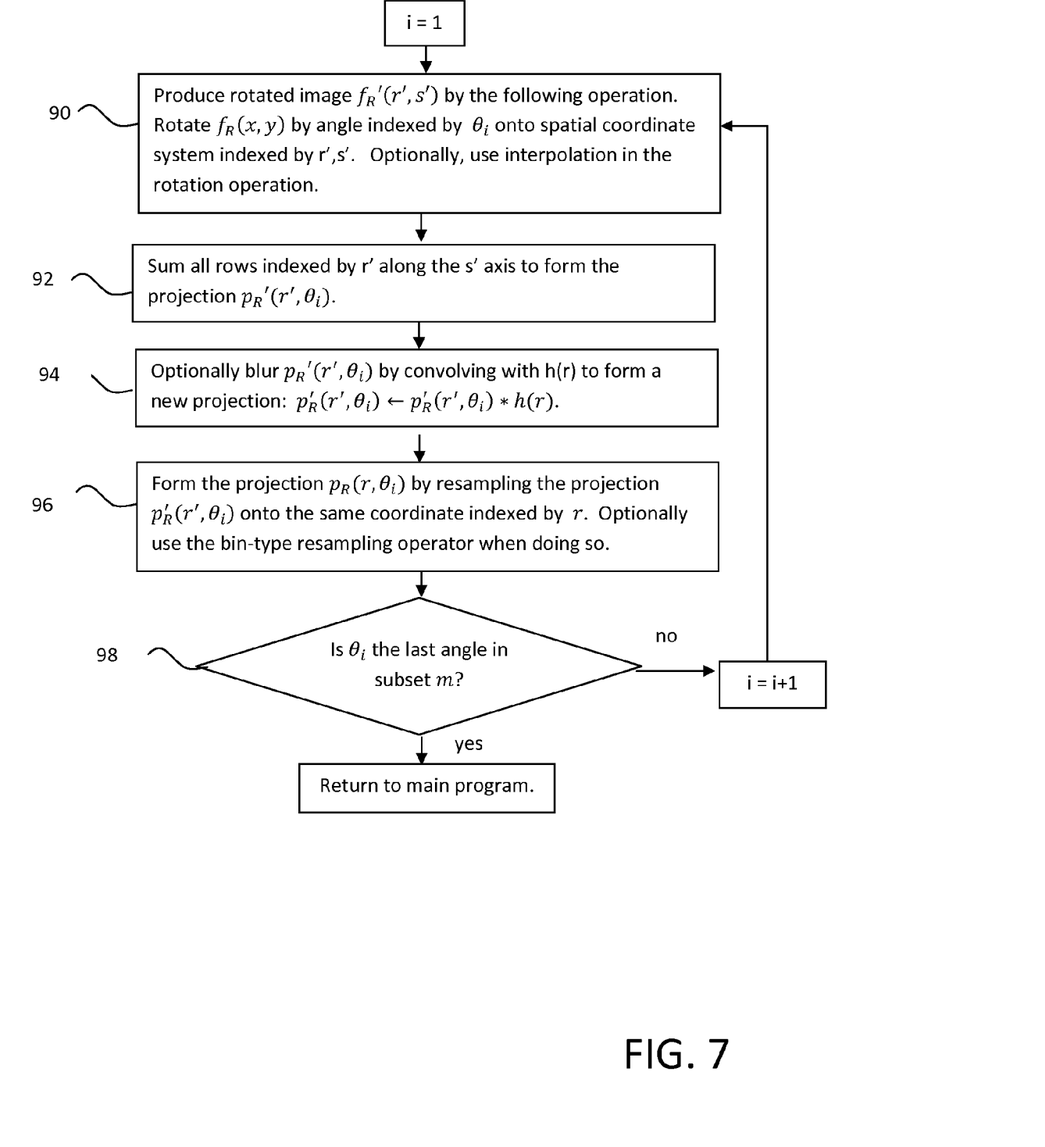
FIG. 7 depicts a scheme for carrying out a projection operator that is part of the flow diagram in FIG. 3.

An embodiment of the projection operator at 76 that includes the smoothing and resampling components is summarized in FIG. 7. The projection is performed for a specific subset $S_m$ of rays indexed by m. FIG. 7 is an illustration that can be used for 2D imaging and parallel beam geometry. A generalized embodiment can be designed and applied to fan-beam, 3D imaging and other geometries. There are many ways to perform a projection besides the one shown in FIG. 7. The set of angle indices $\theta_i$ within the particular subset m are themselves further indexed by i. Under conventional conditions the rotation and sum operations (in 90 and 92) are carried out, as well as the optional interpolation during the rotation. The term interpolation, when used in this document, unless specifically indicated, refers to any of the ways of resampling a signal that are well known by one skilled in the art of signal and image processing. It includes types of linear interpolation (e.g., linear, bilinear, trilinear), spline interpolation (e.g., cubic splines) and nearest neighbor operations where a value of an output resampled signal is taken to be equal to the value of the nearest located sample in the input signal that is being resampled. When super-resolution is desired, optionally, the blur (at 94) and resampling (96) of the projection are carried out. The process is repeated at 98 until all angles are processed.

This projection may be followed by a super-resolution variant of $p_R(r,\theta)$ that is optionally created in which $p_R(r,\theta) \leftarrow p_R(r,\theta) * h_1(r)$ at 76. In this notation, * is the 1D convolution operator and $h_1(r)$ is a representation of the point spread function of the x-ray source and detector system. The $h_1(r)$ function is 1D for 2D CT imaging and the convolution is a 1D convolution with respect to r. The $h_1(r)$ function is 2D for cone-beam 3D imaging, and the convolution may be considered a 2D convolution with respect to the spatial coordinates of the flat-panel sensor illustrated in FIG. 8c and indexed by r. It characterizes the resolution limitation of the CT data-collection system, and may be determined in any manner, e.g., calculated by an analysis of the optics of the system, determined via measurements, determined in an ad hoc or empirical manner including trial-and-error, etc. The notation $\leftarrow$ indicates the replacement operation in the direction of the arrow and implies the words "is replaced by". Even though $h_1(r)$ represents the point-spread function of the x-ray source and detector system, experimentation has shown that, for effective results, the actual $h_1(r)$ that is used may need to be something other than the measured or theoretically determined system point spread function. Sometimes a point spread function that has a different shape, typically having a narrower width than the actual point-spread function, is more effective and results in fewer artifacts in the reconstructed image. For example, a triangle function may be more effective even though the measured $h_1(r)$ may be more like a Gaussian function, and the FWHM of this triangle function may be less than the FWHM of the measured or theoretical Gaussian-like function. An explanation of this behavior is that the projection operation, including interpolation that it uses, and the resampling of $p_R(r,\theta)$ explained later, which also may have interpolation, have an inherent signal smoothing property. Thereby, some of the smoothing that is needed by the convolution is inherent to operations that surround it, so the convolution operator should apply less smoothing than one would expect. These projection and/or smoothing operations are followed by an optional process where the projection $p_R(r,\theta)$ (called the higher resolution projection), is resampled so that the new $p_R(r,\theta)$ (called the lower resolution projection) has an r sample size that matches the size of the r samples in $p(r,\theta)$. There are many ways to do so. An effective way is to form each lower resolution sample by an averaging of neighboring samples in the higher-resolution projection. This averaging is sometimes called binning. However, other schemes will work, including weighted averaging of neighboring sample values, interpolation of neighboring sample values and taking only the value of the nearest neighbor.

The order of the projection and convolution operations may be reversed, since they are linear operations. In one example way of doing so, the current reconstruction $f_R(\bar{x})$ is convolved with a 2D circularly symmetric variant of the PSF according to $f_R(\bar{x}) \leftarrow f_R(\bar{x})  h_1(\bar{x})$, where  indicates 2D convolution. This operation is then followed by the projection of the resulting $f_R(\bar{x})$ to form $p_R(r,\theta)$.

Next at 77, a comparison function $q(r,\theta)$ is calculated for the values of $r,\theta$ that are in the current subset $S_m$. A comparison function dictated by the original EM algorithm is the quotient, $$q(r,\theta) = \frac{p(r,\theta)}{p_R(r,\theta)}.$$

This comparison quantity causes correction factors that, with other operations later in Step xx, iteratively change the reconstructed image. Values of $q(r,\theta)$ above and below 1.0 are caused by values in $f_R(\bar{x})$ that are larger and lower than they should be, respectively, so 1.0 is a sort of desired equilibrium value. The comparison quantity is then back projected onto the array $b(\bar{x})$, at (78), which provides a correction factor to be applied to $f_R(\bar{x})$ by multiplying $f_R(\bar{x})$ with $b(\bar{x})$ at (79).

Depending upon the system and the design of the comparison operation, other values besides 1.0 might be the equilibrium value. For example, with ART, and some variants of the EM algorithm that are founded on gradient ascent principles, the $q(r,\theta)$ cause changes in $f_R(\bar{x})$ by an addition rather than a multiplication, so in these cases the equilibrium value is 0. There are other ways to produce a comparison quantity. Examples include the following possible definitions of $q(r,\theta)$:

$$\frac{p(r,\theta) + \varepsilon_1}{p_R(r,\theta) + \varepsilon_2} \qquad (1)$$

where $\varepsilon_1$ and $\varepsilon_2$ are small constant values and could have the same value. (2) $e^{p(r,\theta) - p_R(r,\theta)}$, where e may be Euler's number or any other constant that could be empirically determined. (3) $p(r,\theta) - p_R(r,\theta)$. (4) Any definition of $q(r,\theta)$ that is further processed to amplify, dampen, smooth or otherwise condition the change it will cause. For example it may be taken to an exponent (e.g., $$(r,\theta) = \left[\frac{p(r,\theta)}{p_R(r,\theta)}\right]^v\!,$$

multiplied by a constant, smoothed or spline fitted. It may have statistical operations applied to it, such as removing outlier values. (5) The many possible comparison functions that are used with other iterative approaches including the ART, MART, EM algorithm variants for transmission CT and alternating minimization/maximization approaches. An optional process that modifies ratio function $q(r,\theta)$ to create a super resolution uses another point spread function $h_2(r)$ function as follows:

$$q(r,\theta) \leftarrow q(r,\theta) * h_2(r).$$

where * denotes the 1D convolution operator * is with respect to the coordinates indexed by r and may be a 1D operation, for 2D imaging, or a 2D operation, for 3D imaging. As with $h_1(\bar{r})$, $h_2(r)$ represents the data-collection system's resolution limit. As with $h_1(\bar{r})$, in order for $h_2(r)$ to be effective, it may need to have a narrower width and a different shape compared to the measured system point-spread function. Experimentation has shown that this convolution operation may not be needed when the projection data contain very little noise. On the other hand, when the projection data contain significant noise, it is an effective way to avoid noise in the reconstructed image. There are other ways to smooth this function to reduce noise because there are many types of data smoothing operators.

Next, at 78, a new image $f_R(\bar{x})$ is generated as $f_R(\bar{x}) \leftarrow b(\bar{x}) f_R(\bar{x})$. The process then loops at 79 for each subset until m=n. When m=n, all of the subsets have been processed, and a determination is made at 80 whether further processing is required. If yes, the program flow loops back to 75 and the sequence of inner iterations repeats. Alternatively, although not shown in FIG. 3, the program flow may loop back to 74 to redefine the subsets, as explained earlier, before re-entering the outer iteration. If no, the process is complete and a final image $f_R(\overline{x})$ is outputted at 81. The determination of whether further processing is required along the outer loop may be done in any manner. For instance, the outer loop may be set to a predetermined number of iterations, e.g., 2. In other cases, an image quality criterion, such as a least-square criterion or a threshold on the I-divergence value, may be calculated.

It is noted that any given outer iteration may not cover all of the values of the r,θ combination, and it may cover certain values more than once.

As mentioned, super-resolution refers to the capability to produce a resolving power that is better than can be achieved by a conventional algorithm. A conventional algorithm is generally considered to involve one of the linear image reconstruction algorithms such as the filtered backprojection or Feldkamp algorithm. Experimentation has shown that even the EM algorithm's original form achieves super-resolution, in this sense, because it does not use a window-function, which is a bandlimiting component operation, that is typical in these linear algorithms. These linear algorithms use a component, called a window function (e.g., Hamming window), that reduces noise, and is one of the determining factors in the resolving power limit. When performing the optional operations for super-resolution, the descriptions here are referring to the capability to improve resolving power beyond what even the typical EM algorithm implementations are capable of.

The following optional processes apply to superresolution that have been mentioned. Any of them may be used separately or in combination to improve resolving power. (1) The pixel size may be optionally set to a value that is smaller than that dictated by conventional criteria. (2) The projection array $p_R(r,\theta)$ at 76 may be optionally blurred using a point-spread function $h_1(r)$. (3) The projection array $p_R(r,\theta)$ may be resampled so that, when the projection is executed it has a sampling with respect to r that matches the pixel size of the image $f_R(\overline{x})$, and after the resampling it has a sampling with respect to r that matches that of the projection array $p(r,\theta)$. (4) The comparison function $q(r,\theta)$ is optionally blurred using point-spread function $h_2(r)$. One reason that Option (1) is not always needed is that the sampling may already be so fine that the resolution limit is already substantially limited by the optics of the data-collection hardware and not by the pixel size. In such cases diminishing returns may result from making the pixel size any smaller. Option (1) is of benefit when the pixel size is a limiting factor of resolving power. A reason that Option (2) is not always needed is that the projection operator has inherent blurring already, since the pixel center locations do not overlay perfectly with the projection ray centers. This inherent blur could explain why the actual point-spread-function may not be the best choice for $h_1(r)$. Since the projection is already inherently blurred, it is thought that the combination of this inherent blur with a narrower point-spread-function produces the overall blur that matches that of the optics. A reason not to choose Option (3) is that one may decide, instead, to produce a preprocessed $p(r,\theta)$ with finer sampling, by resampling the collected $p(r,\theta)$, so that its spatial r sample size matches the pixel size in $f_R(\overline{x})$.

A reason that Option (4) is not always needed is that the backprojection operation is ordinarily carried out using an interpolation operation because the coordinates indexed by r,θ, when overlain on the image pixels as projection rays, do not overlay perfectly onto the centers of the pixels. Interpolation has an inherent blurring character, so it is already implicitly applying part of the blur that is intended by the convolution with $h_2(r)$. This understanding also partly explains why this second convolution may need to use an $h_2(r)$ that is narrower than the actual point spread function of the optics.

Next, the missing data algorithm is described. There are many situations and conditions that would cause data in the projection array $p(r,\theta)$ at certain values or portions of r,θ to be missing, corrupt or unreliable. A detector may be inoperable or producing corrupt output. There are often ways to determine the values of r,θ that have corrupted, missing or invalid values of $p(r,\theta)$. Bad detectors and the values of r,θ that exhibit anomalies corresponding to them can be known by a calibration protocol. The problem can be straightforward to spot in the projection array due to the pattern that it exhibits. It will appear in a sinogram as a sine shaped pattern of zero, near-zero (i.e., dark), or very high (bright) values. When the $p(r,\theta)$ value is considered to be corrupt, missing or invalid, a convenient way of dealing with it is to replace the comparison function, at the given r,θ, with the equilibrium value. This causes the comparison at that index value to be ignored. When super-resolution processing is used in the embodiment of FIG. 3 at 77, this may be accomplished for specific values of r,θ that have corrupt $p(r,\theta)$ as follows.

First, for the given anomalous r,θ values $q(r,\theta)$ is set equal to 1.0 instead of the ratio. This replacement occurs prior to the blur operation at 77. This type of processing has other uses. An object can be so large that portions of it extend outside the range of locations the set of rays traverse. In his case the projection array may be augmented artificially to include extra projection rays traverse the portions of the object that do not fit inside the actual projection rays. In this sense the range of r is extended artificially. These extended rays and their values of r are then treated the same as corrupt data by entering the equilibrium value into their comparison function. In some applications it may be desirable to only reconstruct the image $f_R(\overline{x})$ over a small region of interest, which would be a subset of $\overline{x}$. Doing so may save computation time in 3D imaging situations, compared to reconstructing the whole 3D image, such as with conebeam geometries. There are schemes that can be designed where it saves computation time, as well, in 2D imaging with fan-beam, parallel-beam and hybrids thereof, including Generation 2 (rotate and traverse) geometries. This region-of-interest reconstruction is accomplished by the following steps. The region of interest, which defines a set $\overline{x}$. Values of $p(r,\theta)$ that have their rays traverse the region of interest are treated as valid, and values of $p(r,\theta)$ that do not traverse the region of interested are treated as invalid by entering the equilibrium value into their comparison quantity as described above. Experimentation has shown that this scheme works well by producing an image in the region of interest that is very similar to the image that is produced when the whole image is reconstructed.

All of the concepts and ideas that are presented here are applicable to other iterative algorithms and algorithm approaches besides the EM algorithm. These concepts include all of the approaches and embodiments described above for super-resolution, ordered subsets, corrupt data and so forth. Other iterative algorithms and approaches that these concepts apply to include, for example, those that are referred to as: alternating minimization/maximization, Least squares, penalized least squares, image space reconstruction algorithm, separable paraboloidal surrogates, algebraic reconstruction, multiplicative algebraic reconstruction, EM with Gibbs smoothing, maximum likelihood with penalties, maximum a posteriori assuming priors, Bayesian reconstruction, ML-EM for transmission tomography. Variants will also work for iterative algorithms that assume polyenergetic x-rays and beam hardening, dual energy and related approaches.

As will be appreciated by one skilled in the art, aspects of the present invention may be embodied as a system, method or computer program product. Accordingly, aspects of the present invention may be employed with a computerized process that takes the form of an entirely hardware embodiment, an entirely software embodiment (including firmware, resident software, micro-code, etc.) or an embodiment combining software and hardware aspects that may all generally be referred to herein as a "system." Furthermore, aspects of the present invention may take the form of a computer program product embodied in one or more computer readable medium(s) having computer readable program code embodied thereon. Embodiments of such hardware systems, software and combinations thereof may be include any of the following types of hardware components, some of which execute software code: (1) Field programmable gate arrays (FPGA); (2) Application specific integrated circuits (ASIC's); (3) graphical processing units (GPU's) and mobile GPU's (MGPU's); (4) Discrete digital hardware logic; (5) Digital signal processing (DSP) integrated circuits. In these hardware component examples the devices may be in multiples and operating in parallel, taking advantage of the parallelism and independence of sections of the algorithm calculations. It may include computers, or, clusters of computers that control these hardware components and that are networked to one another.

Any combination of one or more computer readable medium(s) may be utilized. The computer readable medium comprises a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, one or more optical fibers, a portable computer diskette, a hard disk, a random access memory (RAM), a read-only memory (ROM), an erasable programmable read-only memory (EPROM or Flash memory), universal serial port (USB) or Firewire memory stick, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Alternatively, the program product could be embodied on computer readable signal medium which may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language or conventional procedural programming language such as Java, Smalltalk, the "C" programming language or its variants (e.g., C++, C-sharp), Matlab, Basic (including Visual Basic), Python, Compute Unified Device Architecture (CUDA), Open Computing Language (OpenCL), assembler language, machine language, microcode or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer system 10 of FIG. 2 may comprise any type of computing device and is shown including a one or more processors 14, memory 12, an input/output (I/O) 16 (e.g., one or more I/O interfaces and/or devices), and a communications pathway 17. In general, processor(s) 12 execute program code, such as image reconstruction system 18, which is at least partially fixed in memory 16. While executing program code, processor(s) 12 can process data, which can result in reading and/or writing transformed data from/to memory 16 and/or I/O 14 for further processing. Pathway 17 provides a communications link between each of the components in computer system 10. I/O 14 can comprise one or more human I/O devices, which enable a user to interact with computer system 10. To this extent, image reconstruction system 18 can manage a set of interfaces (e.g., graphical user interface(s), application program interface, and/or the like) that enable human and/or system users to interact with the image reconstruction system 18. Further, image reconstruction system 18 can manage (e.g., store, retrieve, create, manipulate, organize, present, etc.) data, such as data in a database, using any solution.

In any event, computer system 10 can comprise one or more general purpose computing articles of manufacture (e.g., computing devices) capable of executing program code. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, configuration management system 18 can be embodied as any combination of system software and/or application software.

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. For example, partial results from an upstream block may be output to the next block for concurrent downstream processing while the upstream block continues to calculate more results—which describes a common technique called pipelining. As further examples, the quotient operation indicated as 77 in FIG. 3 may be inserted within the same loop indexed by i for the projection operation in FIG. 7, and the backprojection at 78 may be decomposed into sub-steps corresponding to each angle which can be inserted into the same loop. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. The finer operations within each block may be implemented in parallel or in other orders as well. For example, the convolution operations in (76, 77) may be realized by a series of well-known sub-operations comprising the fast-Fourier Transform (FFT), which lends well to parallel processing on any of the hardware embodiments explained earlier, such as GPU's.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for reconstructing an image implemented on a computing system, comprising:

inputting a collected projection array $p(r,\theta)$ produced from a computed tomography (CT) system imaging an object defined with a multi-dimensional image function $f(\overline{x})$;

generating an initial reconstructed image $f_R(\overline{x})$;

decomposing indices $r,\theta$ of the collected projection array into a collection of subsets;

utilizing an iterative loop to sequentially process each of the subsets, wherein a processing sequence of the subsets is determined based on an ordered subset criteria, and wherein the process includes:

projecting the reconstructed image $f_R(\overline{x})$ onto a calculated projection array $p_R(r,\theta)$, wherein $r,\theta$ are indices for a current subset;

calculating a comparison quantity $q(r,\theta)$, calculated from a calculated projection array $p_R(r,\theta)$ and the collected projection array $p(r,\theta)$;

backprojecting onto a correction array $b(\overline{x})$ a function that utilizes the comparison quantity $q(r,\theta)$, wherein the comparison quantity is expressed as a ratio with a numerator term being expressed at least in part by a term that contains the collected projection array $p(r,\theta)$ and a denominator term being expressed at least in part by a term that contains reprojected data denoted by a calculated projection array $p_R(r,\theta)$;

generating a correction factor based on the correction array $b(\overline{x})$;

generating a new reconstructed image $f_R(\overline{x})$ that is modified from a previous reconstructed image by an operation involving the correction array $b(\overline{x})$;

wherein the new reconstructed image is enhanced to a finer resolution; and wherein a smoothing operation is applied to a calculated projection array $p_R(r,\theta)$; and outputting a final image $f_R(\overline{x})$.

2. The method of claim 1, wherein the finer resolution is one of:

a significantly finer resolution than a spatial sampling that describes a distance between elements of the collected projection array $p(r,\theta)$; or made finer than an inherent resolving power of the CT system.

3. The method of claim 1, wherein the smoothing operation includes at least one of:

blurring $f_R(\overline{x})$ by convolution prior to the projecting, wherein the convolution is done with a multidimensional point-spread function that is an approximation of a point-spread function of a data-collection system of the CT scanner;

interpolation of a set of values of $f_R(\bar{x})$ onto a set of values of the calculated projection array $p_R(r,\theta)$, wherein the interpolation allows for an inexact mapping of $\bar{x}$ values onto r values during the projecting; and blurring the calculated projection array $p_R(r,\theta)$, after the projecting, by convolution with respect to r with a 1D or 2D point-spread-function that is an approximation of a point-spread function of the data-collection system of the CT scanner.

4. The method of claim 1, further comprising blurring the comparison quantity $q(r,\theta)$ according to at least one of:

interpolation during the backprojection of $q(r,\theta)$ onto $b(\bar{x})$;

blurring $q(r,\theta)$, prior to the backprojection, by convolution with a point-spread function that is an approximation of a point-spread function of a data-collection system of the CT scanner; and blurring $b(\bar{x})$ with a point-spread function that is an approximation of a point-spread function of the data-collection system of the CT scanner.

5. The method of claim 1, wherein the calculated projection $p_R(r,\theta)$ is followed by a resampling so that a modified spatial distance between samples of the calculated projection array match sampling dimensions of the collected projection array $p(r,\theta)$, according to at least one of:

a binning, averaging, interpolation or combination thereof performed in the resampling of $p_R(r,\theta)$; and a nearest-neighbor method performed in the resampling of $p_R(r,\theta)$.

6. The method of claim 1, further comprising:

repeating the iterative loop using an outer loop after each of the subsets have been processed.

7. The method of claim 1, wherein the subsets are defined in such a way that:

a distance between projection angles within individual subsets are substantially maximized; and all projection angles within the subset have a maximum possible distance from all angles within an immediately prior subset in the processing sequence, and have a maximum possible distance from all angles within an immediately subsequent subset in the processing sequence.

8. The method of claim 1, wherein the subsets are defined in such a way that:

a distance between projection angles or projection angles themselves, within individual subsets, are substantially determined from random values.

9. The method of claim 6, wherein the of the subsets is defined by generating a random sequence of integers by way of a pseudo-random number generation algorithm.

10. The method of claim 1, wherein each subset contains just one angle.

11. The method of claim 1, wherein each subset is defined as containing a full complement of possible values of r and a subset of a possible values of $\theta$.

12. The method of claim 6, wherein the subsets, and the number of subsets, are changed before repeating the outer loop.

13. The method of claim 6, wherein repeating the outer loop does not cover a full complement of angles.

14. The method of claim 1, wherein the backprojecting also considers at least one of: effects of attenuation, Beer's law, detection sensitivities, or faulty detectors.

15. The method of claim 1, wherein missing, corrupt, invalid, imprecise, unreliable or undesirable data are handled according to the following:

for values of $r,\theta$ that represent missing, corrupt, invalid, imprecise or undesirable data, the comparison quantity is defined to be equal to a benign value that would occur in an ideal situation where the reprojected data perfectly matches the projection array at $r,\theta$.

16. The method according to claim 15, wherein the projection array has augmented values of r that denote portions of $p(r,\theta)$ that are treated as invalid in order to accommodate a reconstructed image where the object has portions that are not traversed by any real projection rays of the CT scanner.

17. The method of claim 16, wherein a region of interest is reconstructed that has an extent smaller than a whole image, where the following is done:

a set of values of $r,\theta$ whose rays traverse the region of interest are treated as valid; and the set of values of $r,\theta$ whose rays do not traverse the region of interest, are treated as invalid.

18. A program product stored on a non-transitory computer readable storage medium, which when executed by a computer system, reconstructs an image, comprising:

program code for inputting a collected projection array $p(r,\theta)$ produced from a computed tomography (CT) system imaging an object defined with a multi-dimensional image function $f(\bar{x})$;

program code for generating an initial reconstructed image $f_R(\bar{x})$;

program code for decomposing the indices $r,\theta$ of the collected projection array into a collection of subsets;

program code for implementing an iterative loop to sequentially process each of the subsets, wherein a processing sequence of the subsets is determined based on an ordered subset criteria, and wherein the process includes:

projecting the reconstructed image $f_R(\bar{x})$ onto a calculated projection array $p_R(r,\theta)$, wherein $r,\theta$ are indices for a current subset;

calculating a comparison quantity $q(r,\theta)$, calculated from a projection array $p_R(r,\theta)$ and the collected projection array $p(r,\theta)$;

backprojecting onto a correction array $b(\bar{x})$ a function that utilizes the comparison quantity $q(r,\theta)$, wherein the comparison quantity is expressed as a ratio with a numerator term being expressed at least in part by a term that contains the collected projection array $p(r,\theta)$ and a denominator term being expressed at least in part by a term that contains reprojected data of a calculated projection array $p_R(r,\theta)$;

generating a correction factor based on the correction array $b(\bar{x})$;

generating a new reconstructed image $f_R(\bar{x})$ that is modified from a previous reconstructed image using an operation involving the correction array $b(\bar{x})$;

wherein the new reconstructed image is enhanced to a finer resolution; and wherein a smoothing operation is applied to a calculated projection array $p_R(r,\theta)$; and program code for outputting a final image $f_R(\bar{x})$.

19. A computer system for reconstructing an image implemented on a computing system, comprising:

a processor and a memory;

a system for inputting a collected projection array $p(r,\theta)$, produced from a computed tomography (CT) system imaging an object defined with a multi-dimensional image function $f(\bar{x})$;

a system for generating an initial reconstructed image $f_R(\bar{x})$, a system for decomposing indices $r,\theta$ of the collected projection array into a collection of subsets;

a system for utilizing an iterative loop to sequentially process each of the subsets, wherein a processing sequence of the subsets is determined based on an ordered subset criteria, and wherein the process includes:

projecting the reconstructed image $f_R(\bar{x})$ onto a calculated projection array $p_R(r,\theta)$ wherein $r,\theta$ are indices for a current subset;

calculating a comparison quantity $q(r,\theta)$, calculated from a calculated projection array $p_R(r,\theta)$ and the collected projection array $p(r,\theta)$;

backprojecting onto a correction array $b(\bar{x})$, a function that utilizes the comparison quantity $q(r,\theta)$, wherein the comparison quantity is expressed as a ratio with a numerator term being expressed at least in part by a term that contains the collected projection array $p(r,\theta)$ and a denominator term being expressed at least in part by a term that contains reprojected data of a calculated projection array $p_R(r,\theta)$;

generating a correction factor based on the correction array $b(\bar{x})$;

generating a new reconstructed image $f_R(\bar{x})$ that is modified from a previous reconstructed image using an operation involving the correction array $b(\bar{x})$;

wherein the new reconstructed image is enhanced to a finer resolution; and wherein a smoothing operation is applied to a calculated projection array $p_R(r,\theta)$; and a system for outputting a final image $f_R(\bar{x})$.

* * * * *